United States Patent
Jung et al.

(10) Patent No.: US 6,392,077 B1
(45) Date of Patent: May 21, 2002

(54) PROCESS FOR PREPARING ORGANOCHLOROSILANES BY DEHYDROHALOGENATIVE COUPLING REACTION OF ALKYL HALIDES WITH CHLOROSILANES

(75) Inventors: Il-Nam Jung, Songpa-ku; Bok-Ryul Yoo, Kyungki-do; Joon-Soo Han; Seung-Hyun Kang, both of Seoul, all of (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 09/918,446

(22) Filed: Aug. 1, 2001

Related U.S. Application Data

(63) Continuation-in-part of application No. 09/758,344, filed on Jan. 12, 2001, now abandoned.

(30) Foreign Application Priority Data

Nov. 1, 2000 (KR) ............................................. 00-64692

(51) Int. Cl.$^7$ .................................................. C07F 7/08
(52) U.S. Cl. ....................................................... 556/481
(58) Field of Search ......................................... 536/481

(56) References Cited

U.S. PATENT DOCUMENTS 5,182,246 A * 1/1993 Fuchikami et al. ..... 556/481 X
5,508,460 A * 4/1996 Berry et al. ................. 556/481

OTHER PUBLICATIONS

Benkeser, R.A., et al., "Silylation of Organic Halides. A new Method of Forming the Carbon–Silicon Bond", J. Am. Chem. Soc., 91, 3666, (1969).

Furuya, N., et al., "The Condensation Reaction of Trichlorosilane with Allylic Chlorides Catalyzed by Copper Salts in the Presence of a Tertiary Amine", Journal of Organometallic Chemistry, 96, C1–C3, (1975).

Curriu, R.J.P., et al., "Synthesis and Reactivity of Bis(triethoxysilyl)methane, Tris(triethoxysilyl)methane and some Derivatives", Journal of Organometallic Chemistry 562, 79–88 (1998).

* cited by examiner

Primary Examiner—Paul F. Shaver
(74) Attorney, Agent, or Firm—Fitzpatrick, Cella, Harper, & Scinto

(57) ABSTRACT

The present invention relates to a process for preparing organochlorosilanes and more particularly, to the process for preparing organochlorosilanes of $R^4R^3CHSiR^1Cl_2$ (I) by a dehydrohalogenative coupling of hydrochlorosilanes of $HSiR^1Cl_2$ (II) with organic halides of $R^2R^3$ CHX (III) in the presence of quaternary phosphonium salt as a catalyst to provide better economical matter and yield compared with conventional methods, because only a catalytic amount of phosphonium chloride is required and the catalyst can be separated from the reaction mixture and recycled easily.

14 Claims, No Drawings

PROCESS FOR PREPARING
ORGANOCHLOROSILANES BY
DEHYDROHALOGENATIVE COUPLING
REACTION OF ALKYL HALIDES WITH
CHLOROSILANES

This application is a continuation-in-part of U.S. patent application Ser. No. 09/758,344, filed Jan. 12, 2001, now abandoned.

BACKGROUND OF THE INVENTION

1. Field of the Invention

The present invention relates to a process for preparing organochlorosilanes and more particularly, to the process for preparing organochlorosilanes of formula I by a dehydrohalogenative coupling of hydrochlorosilanes of formula II with organic halides of formula III in the presence of quaternary phosphonium salt as a catalyst to provide better economical matter and yield compared with conventional methods, because only catalytic amount of phosphonium chloride is required and the catalyst can be separated from the reaction mixture and recycled easily,

| | |
|---|---|
| $R^4R^3CHSiR^1Cl_2$ | (I) |
| $HSiR^1Cl_2$ | (II) |
| $R^2R^3CHX$ | (III) | wherein $R^1$ represents hydrogen, chloro, or methyl;

X represents chloro or bromo;

$R^2$ is selected from the group consisting of $C_{1-17}$ alkyl, $C_{1-10}$ fluorinated alkyl with partial or full fluorination, $C_{2-5}$ alkenyl, silyl containing alkyl group represented by $(CH_2)_nSiMe_{3-m}Cl_m$ wherein n is an integer of 0 to 2 and m is an integer of 0 to 3, aromatic group represented by $Ar(R')_q$ wherein Ar is $C_{6-14}$ aromatic hydrocarbon, R' is $C_{1-4}$ alkyl, halogen, alkoxy, or vinyl, and q is an integer of 0 to 5, haloalkyl group represented by $(CH_2)_pX$ wherein p is an integer of 1 to 9 and X is chloro or bromo, and aromatic hydrocarbon represented by $ArCH_2X$ wherein Ar is $C_{6-14}$ aromatic hydrocarbons and X is a chloro or bromo;

$R^3$ is hydrogen, $C_{1-6}$ alkyl, aromatic group represented by $Ar(R')_q$ wherein Ar is $C_{6-14}$ aromatic hydrocarbon, R' is $C_{1-4}$ alkyl, halogen, alkoxy, or vinyl, and q is an integer of 0 to 5; and $R^4$ in formula I is the same as $R^2$ in formula III and further, $R^4$ can also be $(CH_2)_pSiR^1Cl_2$ or $ArCH_2SiR^1Cl_2$, when $R^2$ in formula III is $(CH_2)_pX$ or $ArCH_2X$, which is formed from the coupling reaction of $X-(CH_2)_{p+1}-X$ or $XCH_2ArCH_2X$ with the compounds of formula II; or when $R^2$ and $R^3$ are covalently bonded to each other to form a cyclic compounds of cyclopentyl or cyclohexyl group, $R^3$ and $R^4$ are also covalently bonded to each other in the same fashion.

2. Description of the Prior Art

Organochlorosilanes are useful starting materials for silicones. In 1969, Benkeser and co-workers reported that benzyl chloride and benzal chlorides could be silylated with trichlorosilane-tertiary amine 1:1 mixture to give the corresponding trichlorosilyl substituted products by the dehydrochlorinative coupling reaction (Benkeser, R. A.; Gaul, J. M.; Smith, W. E. *J. Am. Chem. Soc.* 1969, 91, 3666).

In 1975, Furuya and Sukawa reported allyltrichlorosilane could be prepared in high yield by a coupling reaction of allyl chloride with a 1:1 mixture of trichlorosilane and tertiary amine in the presence of copper chloride as a catalyst (Furuya, N.; Sukawa, T. *J. Organometal. Chem.* 1975, 96, C1).

Recently, Corriu and co-workers reported that the reaction of chloroform with trichlorosilane in the presence of excess tributylamine gave bis(trichlorosilyl)methane and tris(trichlorosilyl)methane (Corriu, R. J. P.; Granier, M.; Lanneau, G. F. *J. Organometal. Chem.* 1998, 562, 79).

The dehydrochlorinative coupling reaction is a novel method of forming silicon-carbon bonds and useful for the synthesis of organosilicon compounds. Although the dehydrochlorinative coupling reaction of activated alkyl chlorides such as benzyl chloride or allyl chloride have been reported, the coupling reaction of unactivated alkyl chlorides with trichlorosilane has never been reported.

In the previously reports, tertiary amine was used in excess, more than the stoichiometric amount respect to alkyl chloride. The tertiary amine used is a hydrogen chloride scavenger rather than a catalyst. Since the ammonium salt obtained from the tertiary amine and hydrogen chloride has to be neutralized to recycle the amine, it would be too costly to be utilized on a large scale in industry.

It is necessary to find a way to reduce the usage of the amine or find another effective catalyst to apply the coupling reaction for industrial purposes. The present inventors have discovered that a coupling reaction of alkyl halides and hydrochlorosilanes in the presence of tertiary phosphines as a catalyst proceeded to give the corresponding coupled products in good yields by liberating hydrogen halide as a gas at reaction temperatures about 150° C. (Korean Patent Application Number 99-13006(Apr. 13, 1999)). The dehydrohalogenative coupling reaction can be applied to not only the activated alkyl halides such as benzyl chloride or allyl chloride, but also to the unactivated alkyl halides such as n-alkylhexyl chloride or haloalkyl substituted organosilicon compounds. Later the present inventors also discovered that the reaction proceeded to give the coupling products in the presence of tertiary amine as a catalyst instead of tertiary phosphine. However, this reaction gave a little lower yield compared with the tertiary phosphine catalyzed reaction (Korean Patent Application Number 2000-13090(Mar. 15, 2000)).

Although the above processes required only catalytic amount of tertiary phosphine or tertiary amine and are more economically feasible compared with the previous reports, tertiary phosphine and tertiary amine also form complexes with the byproduct of hydrogen chloride and the reactant of alkyl chloride. The complexes have to be neutralized to recycle the catalyst. To solve this problem, we tested many other catalysts and finally found that quaternary phosphonium salts are good catalyst and gave excellent yields.

SUMMARY OF THE INVENTION

It is an object of the present invention to provide new catalysts of quaternary phosphonium salts for the coupling reaction of alkyl halides and hydrochlorosilanes. The quaternary phosphonium salts will not form complexes either with the byproduct of hydrogen chloride or the reactant of alkyl chloride. This will make the separation of the catalyst from the reaction mixture easier and the process more economically feasible for a large scale in industry, because it will not necessary to neutralize the catalyst to recycle.

Other and further objects, features and advantages of the invention will appear more fully from the following description.

DETAILED DESCRIPTION OF THE INVENTION

The present invention relates to processes for preparing the compounds of formula I which comprise a dehydrohalogenative coupling of hydrochlorosilanes of formula II with organic halides of formula III in the presence of quaternary phosphonium salt as a catalyst,

| | |
|---|---|
| $R^4R^3CHSiR^1Cl_2$ | (I) |
| $HSiR^1Cl_2$ | (II) |
| $R^2R^3CHX$ | (III) | wherein $R^1$ represents hydrogen, chloro, or methyl;

X represents chloro or bromo;

$R^2$ is selected from the group consisting of $C_{1-17}$ alkyl, $C_{1-10}$ fluorinated alkyl with partial or full fluorination, $C_{2-5}$ alkenyl, silyl containing alkyl group represented by $(CH_2)_nSiMe_{3-m}Cl_m$ wherein n is an integer of 0 to 2 and m is an integer of 0 to 3, aromatic group represented by $Ar(R')_q$ wherein Ar is $C_{6-14}$ aromatic hydrocarbon, R' is $C_{1-4}$ alkyl, halogen, alkoxy, or vinyl, and q is an integer of 0 to 5, haloalkyl group represented by $(CH_2)_pX$ wherein p is an integer of 1 to 9 and X is chloro or bromo, and aromatic hydrocarbon represented by $ArCH_2X$ wherein Ar is $C_{6-14}$ aromatic hydrocarbons and X is a chloro or bromo;

$R^3$ is hydrogen, $C_{1-6}$ alkyl, aromatic group represented by $Ar(R')_q$ wherein Ar is $C_{6-14}$ aromatic hydrocarbon, R' is $C_{1-4}$ alkyl, halogen, alkoxy, or vinyl, and q is an integer of 0 to 5; and $R^4$ in formula I is the same as $R^2$ in formula III and further, $R^4$ can also be $(CH_2)_pSiRCl_2$ or $ArCH_2SiR^1Cl_2$, when $R^2$ in formula III is $(CH_2)_pX$ or $ArCH_2X$, which is formed from the coupling reaction of $X-(CH_2)_{p+1}-X$ or $XCH_2ArCH_2X$ with the compounds of formula II; or when $R^2$ and $R^3$ are covalently bonded to each other to form a cyclic compounds of cyclopentyl or cyclohexyl group, $R^3$ and $R^4$ are also covalently bonded to each other in the same fashion.

The present invention is described in detail as set forth hereunder.

The coupling reaction of hydrochlorosilanes with organic halides in the present invention can be carried out in most organic solvents such as toluene, hexane, tetrahydrofuran, and acetonitrile, but it also proceeds in neat condition. After sealing the reaction tube with a stainless steel stopper, heating and stirring may be applied for a certain period of time, generally 1 hr to about 48 hours, to complete the reaction. The reaction is carried out at a temperature from 10° C. to 250° C., preferably 130° C. to 200° C.

In a typical preparation, hydrochlorosilanes represented by formula II, organic halides of formula III, solvent, and quaternary phosphonium salt are placed all together in a sealed stainless steel tube under inert atmosphere. The amount of hydrochlorosilane of formula II used is equivalent or more, preferably 2 to 5 folds, relative to the amount of the compounds of formula III. Quaternary phosphonium salt is used as a catalyst in an amount sufficient to catalyze the reaction, generally, 1 to 100 mol %, preferably 3 to 15 mol %, relative to the mole of the compounds of formula III.

After completion of the reaction, hydrocarbon solvents are added to the product mixture to precipitate out the catalyst. The catalyst is filtered and recovered for recycling. The products are distilled under atmospheric pressure or vacuum. It has been reported that when organic phophonium salt immobilized on silicone resins, silica, or zeolite is used, the recovery of the catalyst is more convenient and easier for recycling (Jung, I. N.; Cho, K. D.; Lim, J, C; Yoo, B. R., U.S. Pat. No. 4,613,491).

The chlorosilanes represented by formula II used in this invention may be trichlorosilane, methyldichlorosilane, and dichlorosilane. The organohalogen compounds represented by formula III may be 1-chlorooctane, 1-chloro-3,3,3-trifluoropropane, (chloromethyl)trichlorosilane, (chloromethyl)dichlorosilane, (chloromethyl) trimethylsilane, (3-chloropropyl)trimethylsilane, allyl chloride, allyl bromide, crotyl chloride, benzyl chloride, 4-fluorobenzyl chloride, 4-chlorobenzyl chloride, 4-methoxybenzyl chloride, 4-phenylbenzyl chloride, diphenyl-1-dichloromethane, 1-chloroethylbenzene, cyclopentyl chloride, 2-chlorobutane, isopropyl chloride, dichloromethane, 1,2-dichloroethane, 1,3-dichloropropane, 1-bromo-3-chloropropane, 1,4-dichlorobutane, and 1,4-bis (chloromethyl)benzene.

The catalyst of quaternary phosphonium salts may be represented by the following formula IV, $$PR''_4X' \qquad (IV)$$

wherein X' is chloro, bromo or iodo; and R" is selected from $C_{1-12}$ alkyl, $C_{1-6}$ alkyl substituted aromatic and phenyl group or two R" can be covalently bonded to each other to form a cyclic compound where each R" is independently selected therefrom.

The catalyst can also be represented by the following formula V, $$X'R''_3P-Y-PR''_3X' \qquad (V)$$

wherein X' and R" are defined as above; and Y can be $C_{1-12}$ alkyl or aromatic group optionally containing alkyls.

The above catalysts can be used in an immobilized form on a silicon resin, silica, inorganic supporter or organic polymer.

The catalysts represented by formula IV and V used in this invention may be benzyltributylphosphonium chloride, tetrabutylphosphonium chloride, tetramethylphosphonium chloride, tetraethylphosphonium chloride, benzyltriphenylphosphonium chloride, ethylene bis (benzyldimethylphosphonium chloride), or immobilized quarternary phosphonium chloride on silica, silicone resin, inorganic supporter or organic polymer.

The invention will be further illustrated by the following examples. It is, however, not intended that this invention will be limited by the examples.

EXAMPLE 1

Reaction of 1-Chlorooctane and Trichlorosilane in the Presence of Benzyltributylphosphonium Chloride In a 25 ml oven dried stainless steel tube, 0.22 g (0.67 mmol) of benzyltributylphosphonium chloride, 1.00 g (6.73 mmol) of 1-chlorooctane, and 2.71 g (20.0 mmol) of trichlorosilane were added under a dry nitrogen atmosphere. After sealing the cylinder with a cap, the reactor was maintained at 170° C. for 2 hrs. The resulting mixture was distilled to yield 1.45 g of n-octyltrichlorosilane (yield; 87%).

n-Octyltrichlorosilane; MS (70eV EI) m/z (relative intensity): 250(1), 248(3), 246(4), 179(12), 177(35), 175 (34), 135(53), 133(54), 85(100), 71(57), 57(98).

EXAMPLE 2

Reaction of 1-Chlorooctane and Trichlorosilane in the Presence of Tetrabutylphosphonium Chloride In the same apparatus and procedure as Example 1 above, 0.20 g (0.68 mmol) of tetrabutylphosphonium chloride, 1.00 g (6.73 mmol) of 1-chlorooctane and 2.71 g (20.0 mmol) of trichlorosilane were reacted at 170° C. for 2 hrs. The resulting mixture was distilled to give 1.42 g of n-octyltrichlorosilane (yield; 85%).

EXAMPLE 3

Reaction of 1-Chloro-3,3,3-Trifluoropropane and Trichlorosilane in the Presence of Tetrabutylphosphonium Chloride In the same apparatus and procedure as Example 1 above, 0.20 g (0.68 mmol) of tetrabutylphosphonium chloride, 0.89 g (6.72 mmol) of 1-chloro-3,3,3-trifluoropropane, and 2.71 g (20.0 mmol) of trichlorosilane were reacted at 150° C. for 10 hrs. The resulting mixture was distilled to give 1.24 g of (3,3,3-trifluoropropyl)trichlorosilane (yield; 80%).

(3,3,3-Trifluoropropyl)trichlorosilane; MS (70eV ED) m/z (relative intensity): 137(24), 135(71), 133(72), 98(11), 78(87), 77(100), 69(20), 63(21), 59(26), 51(11).

EXAMPLE 4

Reaction of (Chloromethyl)trichlorosilane and Trichlorosilane in the Presence of Benzyltributylphosphonium Chloride In the same apparatus and procedure as Example 1 above, 0.22 g (0.67 mmol) of benzyltributylphosphonium chloride, 1.23 g (6.69 mmol) of (chloromethyl)trichlorosilane, and 2.71 g (20.0 mmol) of trichlorosilane were reacted at 160° C. for 15 hrs. The resulting mixture was distilled to give 1.13 g of 1,1,1,3,3,3-hexachloro-1,3-disilapropane (yield; 68%).

1,1,1,3,3,3-Hexachloro-1,3-disilapropane; H-NMR ($CDCl_3$, ppm): δ 1.87 (s, $SiCH_2Si$).

EXAMPLE 5

Reaction of (Chloromethyl)methyldichlorosilane and Trichlorosilane in the Presence of Tetrabutylphosphonium Chloride In the same apparatus and procedure as Example 1 above, 0.18 g (0.61 mmol) of tetrabutylphosphonium chloride, 1.00 g (6.12 mmol) of (chloromethyl)methyldichlorosilane, and 2.52 g (18.6 mmol) of trichlorosilane were reacted at 150° C. for 2 hrs. The resulting mixture was distilled to give 0.96 g of 1,1,1,3,3-pentachloro-1,3-disilabutane (yield; 60%).

1,1,1,3,3,-Pentachloro-1,3-disilabutane; H-NMR ($CDCl_3$, ppm): δ 6 0.94 (s, 3H, $SiCH_3$), 1.58 (s, $SiCH_2Si$).

EXAMPLE 6

Reaction of (Chloromethyl)dimethylchlorosilane and Trichlorosilane in the Presence of Tetrabutylphosphonium Chloride In the same apparatus and procedure as Example 1 above, 0.27 g (1.5 mmol) of tetrabutylphosphonium chloride, 2.15 g (15.0 mmol) of (chloromethyl)dimethylchlorosilane, and 6.10 g (45.0 mmol) of trichlorosilane were reacted at 150° C. for 10 hrs. The resulting mixture was distilled to give 2.18 g of 1,1,1,3-tetrachloro-3-methyl-1,3-disilabutane (yield; 60%).

1,1,1,3-Tetrachloro-3-methyl-1,3-disilabutane; H-NMR ($CDCl_3$, ppm): δ 0.62 (s, 6H, $SiCH_3$), 1.28 (s, 2H, $SiCH_2Si$).

EXAMPLE 7

Reaction of (Chloromethyl)trimethylsilane and Trichlorosilane in the Presence of Benzyltriphenylphosphonium Chloride In the same apparatus and procedure as Example 1 above, 0.29 g (0.75 mmol) of benyltriphenylphosphonium chloride, 0.92 g (7.5 mmol) of (chloromethyl)trimethylsilane, and 3.05 g (22.5 mmol ) of trichlorosilane were reacted at 150° C. for 10 hrs. The resulting mixture was distilled to give 1.20 g of 1,1,1-trichloro-3,3-dimethyl-1,3-disilabutane (yield; 72%).

1,1,1-Trichloro-3,3-dimethyl-1,3-disilabutane; H-NMR ($CDCl_3$, ppm): δ 0.25 (s, 9H, $SiCH_3$), 0.85 (s, 2H, $SiCH_2Si$).

EXAMPLE 8

Reaction of (3-Chloropropyl)trimethylsilane and Trichlorosilane in the Presence of Tetrabutylphosphonium Chloride In the same apparatus and procedure as Example 1 above, 0.22 g (0.75 mmol) of tetrabutylphosphonium chloride, 1.13 g (7.50 mmol) of (3-chloropropyl)trimethylsilane, and 3.05 g (22.5 mmol) of trichlorosilane were reacted at 150° C. for 10 hrs. The resulting mixture was distilled to give 1.57 g of [(3-trichlorosilyl)propyl]trimethylsilane (yield; 84%).

[(3-trichlorosilyl)propyl]trimethylsilane; H-NMR ($CDCl_3$, ppm): δ 0.02 (s, 9H, $SiCH_3$), 0.66 (m, 2H, $Me_3SiCH_2$), 1.47 (m, 2H, $CH_2$), 1.61 (m, 2H, $CH_2SiCl_3$).

EXAMPLE 9

Reaction of Allyl Chloride and Trichlorosilane in the Presence of Tetramethylphosphonium Chloride In the same apparatus and procedure as Example 1 above, 0.16 g (1.3 mmol) of tetramethylphosphonium chloride, 1.00 g (13.1 mmol) of allyl chloride, and 5.31 g (39.2 mmol) of trichlorosilane were reacted at 150° C. for 2 hrs. The resulting mixture was distilled to give 1.72 g of allyltrichlorosilane (yield; 75%).

Allyltrichlorosilane; H-NMR ($CDCl_3$, ppm): 2.35–2.37 (d, 2H, $CH_2$), 5.18–5.24 (m, 2H, $CH_2$=), 5.71–5.85 (m, 1H, CH=).

EXAMPLE 10

Reaction of Allyl Chloride and Trichlorosilane in the Presence of Immobilized Quaternary Phosphonium Chloride Catalyst In the same apparatus and procedure as Example 1 above, 0.30 g of quaternary phosphonium chloride containing silicon resin [$(RSiO_{3/2})_n$, R={3-(tributylphosphonium)propyl} chloride], 1.00 g (13.1 mmol) of allyl chloride, and 5.31 g (39.2 mmol) of trichlorosilane were reacted at 150° C. for 2 hrs. The resulting mixture was distilled to give 1.20 g of allyltrichlorosilane (yield; 52%).

EXAMPLE 11

Reaction of Allyl Chloride and Methyldichlorosilane in the Presence of Tetraethylphosphonium Chloride In the same apparatus and procedure as Example 1 above, 0.24 g (1.31 mmol) of tetraethylphosphonium chloride, 1.00 g (13.1 mmol) of allyl chloride, and 4.52 g (39.3 mmol) of methyldichlorosilane were reacted at 150° C. for 2 hrs. The resulting mixture was distilled to give 0.45 g of allylmethyldichlorosilane (yield; 22%).

Allylmethyldichlorosilane; MS (70eV EI) m/z (relative intensity): 156(13), 154(18), 141(13), 139(20), 117(13), 115(70), 114(9), 113(100), 65(7), 63(22).

EXAMPLE 12

Reaction of Allyl Chloride and Dichlorosilane in the Presence of Tetrabutylphosphonium Chloride In the same apparatus and procedure as Example 1 above, 0.36 g (1.22 mmol) of tetrabutylphosphonium chloride, 0.94 g (12.3 mmol) of allyl chloride, and 6.22 g (61.6 mmol) of dichlorosilane were reacted 150° C. for 1 hr. The resulting mixture was distilled to give 0.38 g of allyldichlorosilane (yield; 22%) and 0.32 g of allyltrichlorosilane (yield; 15%).

Allyldichlorosilane; H-NMR (CDCl$_3$, ppm): δ 2.17–2.19 (d, 2H, SiCH$_2$), 5.13–5.18 (m, 2H, CH$_2$=), 5.47 (t, J=1.8 Hz, 1H, SiH), 5.71–5.85 (m, 1H, CH=).

EXAMPLE 13

Reaction of Allyl Bromide and Trichlorosilane in the Presence of Tetramethylphosphonium Bromide In the same apparatus and procedure as Example 1 above, 0.21 g (1.2 mmol) of tetramethylphosphonium bromide, 1.50 g (12.4 mmol) of allyl bromide, and 5.04 g (37.2 mmol) of trichlorosilane were reacted at 150° C. for 2 hrs. The resulting mixture was distilled to give 1.85 g of allyltrichlorosilane (yield; 85%).

EXAMPLE 14

Reaction of Crotyl Chloride and Trichlorosilane in the Presence of Tetrabutylphosphonium Chloride In the same apparatus and procedure as Example 1 above, 0.32 g (1.1 mmol) of tetrabutylphosphonium chloride, 1.00 g (11.0 mmol) of crotyl chloride, and 4.47 g (33.0 mmol) of trichlorosilane were reacted at 130° C. for 1 hr. The resulting mixture was distilled to give 1.04 g of crotyltrichlorosilane (yield; 50%).

Crotyltrichlorosilane; MS (70eV EI) m/z (relative intensity): 190(7), 188(7), 135(10), 133(10), 63(7), 56(6), 55(100), 54(11), 54(11), 53(8).

EXAMPLE 15

Reaction of Benzyl Chloride and Trichlorosilane in the Presence of Tetrabutylphosphonium Chloride In the same apparatus and procedure as Example 1 above, 0.23 g (0.78 mmol) of tetrabutylphosphonium chloride, 1.00 g (7.90 mmol) of benzyl chloride, and 3.21 g (23.7 mmol) of trichlorosilane were reacted at 130° C. for 4 hrs. The resulting mixture was distilled to give 1.48 g of benzyltrichlorosilane (yield; 83%).

Benzyltrichlorosilane; H-NMR (CDCl$_3$, ppm): δ 2.92 (s, 2H, CH$_2$), 7.29–7.36 (m, 5H, ArH).

EXAMPLE 16

Reaction of Benzyl Chloride and Trichlorosilane in the Presence of Benzyltributylphosphonium Chloride In the same apparatus and procedure as Example 1 above, 0.26 g (0.79 mmol) of benzyltributylphosphonium chloride, 1.00 g (7.90 mmol) of benzyl chloride, and 3.21 g (23.7 mmol) of trichlorosilane were reacted at 150° C. for 2 hrs. The resulting mixture was distilled to give 1.43 g of benzyltrichlorosilane (yield; 80%).

EXAMPLE 17

Reaction of Benzyl Chloride and Trichlorosilane in the Presence of Benzyltriphenylphosphonium Chloride In the same apparatus and procedure as Example 1 above, 0.31 g (0.80 mmol) of benzyltriphenylphosphonium chloride, 1.00 g (7.90 mmol) of benzyl chloride, and 3.21 g (23.7 mmol) of trichlorosilane were reacted at 150 ° C. for 3 hrs. The resulting mixture was distilled to give 0.07 g of benzyltrichlorosilane (yield; 4%).

EXAMPLE 18

Reaction of Benzyl Chloride and Trichlorosilane in the Presence of Ethylenebis (benzyldimethylphosphonium Chloride)

In the same apparatus and procedure as Example 1 above, 0.16 g (0.40 mmol) of ethylenebis (benzyldimethylphosphonium chloride), 1.00 g (7.90 mmol) of benzyl chloride, and 3.21 g (23.7 mmol) of trichlorosilane were reacted at 150° C. for 2 hrs. The resulting mixture was distilled to give 1.51 g of benzyltrichlorosilane (yield; 85%).

EXAMPLE 19

Reaction of Benzyl Chloride and Methyldichlorosilane in the Presence of Benyltributylphosphonium Chloride In the same apparatus and procedure as Example 1 above, 0.26 g (0.79 mmol) of benyltributylphosphonium chloride, 1.00 g (7.90 mmol) of benzyl chloride, and 2.73 g (23.7 mmol) of methyldichlorosilane were reacted at 200° C. for 2 hrs. The resulting mixture was distilled to give 0.39 g of benzylmethyldichlorosilane (yield; 24%).

Benzylmethyldichlorosilane; H-NMR (CDCl$_3$, ppm): δ 0.96 (s, 3H, SiCH$_3$), 2.85 (s, 2H, CH$_2$), 7.29–7.36 (m, 5H, ArH).

EXAMPLE 20

Reaction of Benzyl Chloride and Dichlorosilane in the Presence of Benyltributylphosphonium Chloride In the same apparatus and procedure as Example 1 above, 0.26 g (0.79 mmol) of benyltributylphosphonium chloride, 1.01 ml (7.98 mmol) of benzyl chloride, and 2.42 g (24.0 mmol) of dichlorosilane were reacted at 150° C. for 2 hrs. The resulting mixture was distilled to give 0.29 g of benzyldichlorosilane (yield; 19%) and 0.95 g of benzyltrichlorosilane (yield; 53%).

Benzyldichlorosilane; H-NMR (CDCl$_3$, ppm): δ 2.76 (s, J=2.0 Hz, 2H, CH$_2$), 5.54 (t, J=2.0 Hz, 1H, SiH), 7.18–7.37 (m, 5H, ArH).

EXAMPLE 21

Reaction of 4-Fluorobenzyl Chloride and Trichlorosilane in the Presence of Tetrabutylphosphonium Chloride In the same apparatus and procedure as Example 1 above, 0.20 g (0.68 mmol) of tetrabutylphosphonium chloride, 1.00 g (6.92 mmol) of 4-fluorobenzyl chloride, and 2.80 g (20.7 mmol) of trichlorosilane were reacted at 130° C. for 4 hrs. The resulting mixture was distilled to give 1.19 g of (4-fluorobenzyl)trichlorosilane (82%).

(4-Fluorobenzyl)trichlorosilane; H-NMR (CDCl$_3$, ppm): δ 2.89 (s, 2H, —CH$_2$—), 7.00–7.20 (m, 4H, ArH).

EXAMPLE 22

Reaction of 4-Chlorobenzyl Chloride and Trichlorosilane in the Presence of Tetrabutylphosphonium Chloride In the same apparatus and procedure as Example 1 above, 0.22 g (0.75 mmol) of tetrabutylphosphonium chloride, 1.21 g (7.51 mmol) of 4-chlorobenzyl chloride, and 3.05 g (22.5 mmol) of trichlorosilane were reacted at 130° C. for 4 hrs. The resulting mixture was distilled to give 1.37 g of (4-chlorobenzyl)trichlorosilane (yield; 81%).

(4-Chlorobenzyl)trichlorosilane; H-NMR (CDCl$_3$, ppm): δ 2.93 (s, 2H, —CH$_2$—), 7.29–7.38 (m, 4H, ArH).

EXAMPLE 23

Reaction of 4-Methoxybenzyl Chloride and Trichlorosilane in the Presence of Tetrabutylphosphonium Chloride In the same apparatus and procedure as Example 1 above, 0.19 g (0.64 mmol) of tetrabutylphosphonium chloride, 1.00 g (6.39 mmol) of 4-methoxybenzyl chloride, and 2.46 ml (18.2 mmol) of trichlorosilane were reacted at 130° C. for 4 hrs. The resulting mixture was distilled to give 1.22 g of (4-methoxybenzyl)trichlorosilane (yield; 86%).

(4-Methoxybenzyl)trichlorosilane; MS(70eV EI) m/z (relative intensity): 256(7), 254(7), 135(5), 133(5), 122(9), 121(100), 78(10), 77(8),

EXAMPLE 24

Reaction of 4-Phenylbenzyl Chloride and Trichlorosilane in the Presence of Tetrabutylphosphonium Chloride In the same apparatus and procedure as Example 1 above, 0.22 g (0.75 mmol) of tetrabutylphosphonium chloride, 1.52 g (7.5 mmol) of 4-phenylbenzyl chloride, 10 ml of dried benzene, and 3.05 g (22.5 mmol) of trichlorosilane were reacted at 150° C. for 2 hrs. The resulting mixture was distilled to give 1.70 g of (4-phenylbenzyl)trichlorosilane (yield; 85%).

(4-Phenylbenzyl)trichlorosilane; H-NMR (CDCl$_3$, ppm): δ 2.90 (s, 2H, CH$_2$), 7.20–7.40 (m, 9H, ArH).

EXAMPLE 25

Reaction of Isopropyl Chloride and Trichlorosilane in the Presence of Tetrabutylphosphonium Chloride In the same apparatus and procedure as Example 1 above, 0.37 g (1.25 mmol) of tetrabutylphosphonium chloride, 1.00 g (12.73 mmol) of isopropyl chloride, and 5.17 g (38.20 mmol) of trichlorosilane were reacted at 180° C. for 13 hrs. The resulting mixture was distilled to give 1.72 g of isopropyltrichlorosilane (yield; 76%).

Isopropyltrichlorosilane; H-NMR (CDCl$_3$, ppm): δ 1.17–1.20 (d, 6H, (CH$_3$)$_2$CH—, CH$_3$), 1.49–1.58 (m, 9H, —CHSiCl$_3$).

EXAMPLE 26

Reaction of 2-Chlorobutane and Trichlorosilane in the Presence of Tetrabutylphosphonium Chloride In the same apparatus and procedure as Example 1 above, 0.32 g (1.09 mmol) of tetrabutylphosphonium chloride, 1.00 g (10.90 mmol) of 2-chlorobutane, and 4.43 g (32.71 mmol) of trichlorosilane were reacted at 180° C. for 13 hrs. The resulting mixture was distilled to give 0.82 g of 2-trichlorosilyl butane (yield; 39%).

2-Trichlorosilylbutane; MS (70eV); m/z (relative intensity): 190(2), 139(4), 137(6), 135(16), 133(16), 98(4), 63(6), 57(100), 56(19), 41(25), 39(7).

EXAMPLE 27

Reaction of Cyclopentyl Chloride and Trichlorosilane in the Presence of Tetrabutylphosphonium Chloride In the same apparatus and procedure as Example 1 above, 0.29 g (0.98 mmol) of tetrabutylphosphonium chloride, 1.01 g (9.66 mmol) of cyclopentyl chloride, and 3.92 g (28.94 mmol) of trichlorosilane were reacted at 180° C. for 8 hrs. The resulting mixture was distilled to give 0.43 g cyclopentyltrichlocorosilane (yield; 22%).

Cyclopentyltrichlocorosilane; MS (70eV EI) m/z (relative intensity): 202(2), 176(11), 174(11), 135(14), 133(14), 69(100), 68(23), 67(14), 65(4), 63(5).

EXAMPLE 28

Reaction of 1-Chloroethylbenzene and Trichlorosilane in the Presence of Tetrabutylphosphonium Chloride In the same apparatus and procedure as Example 1 above, 0.20 g (0.68 mmol) of tetrabutylphosphonium chloride, 0.96 g (6.83 mmol) of 1-chloroethylbenzene, and 2.71 g (20.00 mmol) of trichlorosilane were reacted at 150° C. for 6 hrs. The resulting mixture was distilled to give 0.58 g 1-trichlorosilylethylbenzene (yield; 35%).

1-Trichlorosilylethylbenzene; MS (70eV EI) m/z (relative intensity): 238(10), 133(5), 106(12), 105(100), 103(10), 79(12), 77(14), 63(5), 51(6).

EXAMPLE 29

Reaction of Diphenyl-1-chloromethane and Trichlorosilane in the Presence of Tetrabutylphosphonium Chloride In the same apparatus and procedure as Example 1 above, 0.14 g (0.47 mmol) of tetrabutylphosphonium chloride, 0.95 g (4.69 mmol) of 1-chloroethylbenzene, and 1.91 g (14.10 mmol) of trichlorosilane were reacted at 150° C. for 6 hrs. The resulting mixture was distilled to give 0.31 g diphenyl-1-trichlorosilylmethane (yield; 22%).

Diphenyl-1-trichlorosilylmethane; MS (70eV EI) m/z (relative intensity): 300(8), 168(17), 167(100), 166(15), 165(39), 152(18), 133(3), 115(4), 63(5).

EXAMPLE 30

Reaction of Dichloromethane and Trichlorosilane in the Presence of Tetrabutylphosphonium Chloride In the same apparatus and procedure as Example 1 above, 0.44 g (1.50 mmol) of tetrabutylphosphonium chloride, 0.64 g (7.5 mmol) of dichloromethane, and 10.16 g (75.0 mmol) of trichlorosilane were reacted at 150° C. for 6 hrs. The resulting mixture was distilled to give a small amount of bis(trichlorosilyl)methane.

Bis(trichlorosilyl)methane; H-NMR (CDCl$_3$, ppm): δ 1.59 (s, SiCH$_2$).

EXAMPLE 31

Reaction of 1,2-Dichloroethane and Trichlorosilane in the Presence of Tetrabutylphosphonium Chloride In the same apparatus and procedure as Example 1 above, 0.44 g (1.50 mmol) of tetrabutylphosphonium chloride, 0.74 g (7.5 mmol) of 1,2-dichloroethane, and 10.16 g (75.0 mmol) of trichlorosilane were reacted at 150° C. for 10 hrs. The resulting mixture was distilled to give 1.09 g of 1,2-bis(trichlorosilyl)ethane (yield; 54%).

1,2-Bis(trichlorosilyl)ethane; H-NMR (CDCl$_3$, ppm): δ 1.59 (s, 4H, SiCH$_2$).

EXAMPLE 32

Reaction of 1,3-Dichloropropane and Trichlorosilane in the Presence of Tetrabutylphosphonium Chloride In the same apparatus and procedure as Example 1 above, 0.44 g (1.50 mmol) of tetrabutylphosphonium chloride, 0.85 g (7.5 mmol) of 1,3-dichloropropane, and 10.16 g (75.0 mmol) of trichlorosilane were reacted at 150° C. for 10 hrs. The resulting mixture was distilled to give 1.68 g of 1,3-bis(trichlorosilyl)propane (yield; 72%) and 0.22 g of (3-chloropropyl)trichlorosilane (yield; 14%).

1,3-Bis(trichlorosilyl)propane; H-NMR (CDCl$_3$, ppm): δ 1.56 (m, 4H, SiCH$_2$), 1.92 (m, 2H, CH$_2$). 3-(Chloropropyl)trichlorosilane; H-NMR (CDCl$_3$, ppm): δ 1.58 (m, 2H, SiCH$_2$), 2.06 (m, 2H, CH$_2$), 3.61 (t, J=6.48, 2H, CH$_2$Cl).

EXAMPLE 33

Reaction of 1-Bromo-3-chloropropane and Trichlorosilane in the Presence of Tetrabutylphosphonium Chloride In the same apparatus and procedure as Example 1 above, 0.44 g (1.50 mmol) of tetrabutylphosphonium chloride, 1.18 g (7.50 mmol) of 1-bromo-3-chloropropane, and 10.16 g (75.0 mmol) of trichlorosilane were reacted at 150° C. for 4 hrs. The resulting mixture was distilled to give 1.21 g of 1,3-bis(trichlorosily)propane (yield; 52%), 0.17 g of 3-(bromopropyl)trichlorosilane (yield; 9%), and 0.16 g of 3-(chloropropyl)trichlorosilane (yield; 10%).

EXAMPLE 34

Reaction of 1,4-Dichlorobutane and Trichlorosilane in the Presence of Tetrabutylphosphonium Chloride In the same apparatus and procedure as Example 1 above, 0.44 g (1.50 mmol) of tetrabutylphosphonium chloride, 0.95 g (7.5 mmol) of 1,4-dichlorobutane, and 10.16 g (75.0 mmol) of trichlorosilane were reacted at 150° C. for 20 hrs. The resulting mixture was distilled to give 2.02 g of 1,4-bis(trichlorosilyl)butane (yield; 83%).

1,4-Bis(trichlorosilyl)butane; H-NMR (CDCl$_3$, ppm): δ 1.46 (m, 4H, SiCH$_2$), 1.73 (m, 4H, CH$_2$).

EXAMPLE 35

Reaction of 1,4-Bis(chloromethyl)benzene and Trichlorosilane in the Presence of Tetrabutylphosphonium Chloride In the same apparatus and procedure as Example 1 above, 0.059 g (0.20 mmol) of tetrabutylphosphonium chloride, 0.35 g (2.0 mmol) of 1,4-bis(chloromethyl)benzene, 1.35 g (10.0 mmol) of trichlorosilane, and 10 ml of dried benzene were reacted at 150° C. for 2 hrs. The resulting mixture was distilled to give 0.16 g of 1-chloromethyl-4-(trichlorosilylmethyl)benzene (yield; 30%) and 0.19 g of 1,4-bis(trichlorosilylmethyl)benzene (yield; 25%).

1-Chloromethyl-4-(trichlorosilylmethyl)benzene; MS (70eV EI) m/z (relative intensity): 274(23), 272(17), 241 (37), 239(99), 238(17), 237(100), 139(33), 104(39), 103 (32), 77(20). 1,4-Bis(trichlorosilylmethyl)benzene; MS (70eV EI) m/z (relative intensity): 372(15), 241(38), 240 (16), 239(99), 238(17), 237(100), 134(13), 132(14), 104 (27), 103(19).

Having now fully described the present invention, it will be apparent to one of ordinary skill in the art that many changes and modifications can be made thereto without departing from the spirit of scope of the invention as set forth herein.

What is claimed is:

1. A process for preparing organosilicon compounds represented by formula I, comprising a dehydrohalogenative coupling reaction of hydrochlorosilane represented by formula II with organic halides represented by formula III in the presence of quaternary phosphonium salt as a catalyst,

| | |
|---|---|
| $R^4R^3CHSiR^1Cl_2$ | (I) |
| $HSiR^1Cl_2$ | (II) |
| $R^2R^3CHX$ | (III) | wherein $R^1$ represents hydrogen, chloro, or methyl;

X represents chloro or bromo;

$R^2$ is selected from the group consisting of $C_{1-17}$ alkyl, $C_{1-10}$ fluorinated alkyl with partial or full fluorination, $C_{2-5}$ alkenyl, silyl containing alkyl group represented by $(CH_2)_nSiMe_{3-m}Cl_m$ wherein n is an integer of 0 to 2 and m is an integer of 0 to 3, aromatic group represented by $Ar(R')_q$ wherein Ar is $C_{6-14}$ aromatic hydrocarbon, R' is $C_{1-14}$ alkyl, halogen, alkoxy, or vinyl, and q is an integer of 0 to 5, haloalkyl group represented by $(CH_2)_pX$ wherein p is an integer of 1 to 9 and X is chloro or bromo, and aromatic hydrocarbon represented by $ArCH_2X$ wherein Ar is $C_{6-14}$ aromatic hydrocarbons and X is a chloro or bromo;

$R^3$ is hydrogen, $C_{1-6}$ alkyl, aromatic group represented by $Ar(R')_q$ wherein Ar is $C_{6-14}$ aromatic hydrocarbon, R' is $C_{1-4}$ alkyl, halogen, alkoxy, or vinyl, and q is an integer of 0 to 5; and $R^4$ in formula I is the same as $R^2$ in formula III and further, $R^4$ can also be $(CH_2)_pSiR^1Cl_2$ or $ArCH_2SiR^1Cl_2$, when $R^2$ in formula III is $(CH_2)_pX$ or $ArCH_2X$, which is formed from the coupling reaction of $X$-$(CH_2)_{p+1}$-$X$ or $XCH_2ArCH_2X$ with the compounds of formula II; or when $R^2$ and $R^3$ are covalently bonded to each other to form a cyclic compounds of cyclopentyl or cyclohexyl group, $R^3$ and $R^4$ are also covalently bonded to each other in the same fashion.

2. The process for preparing organosilicon compounds according to claim 1, wherein said catalyst has the following formula IV,

| | |
|---|---|
| $PR''_4X'$ | (IV) |

wherein X' is chloro, bromo, or iodo; and two R'' can be covalently bonded to each other to form a cyclic compounds and each R'' is independently selected from a $C_{1-12}$ alkyl, $C_{1-6}$ alkyl substituted aromatics, or phenyl groups.

3. The process for preparing organosilicon compounds according to claim 1, wherein said catalyst has the following general formula (V),

| | |
|---|---|
| $X'R''_3P$-$Y$-$PR''_3X'$ | (V) |

wherein X' is chloro, bromo, or iodo; Y is selected from a $C_{1-12}$ alkyl and optionally alkyl substituted aromatic; and two R'' can be covalently bonded to each other to form a cyclic compounds and each R'' is independently selected from a $C_{1-12}$ alkyl, $C_{1-6}$ alkyl substituted aromatics and phenyl groups.

4. The process for preparing organosilicon compounds according to any one of claims 1, 2, or 3, wherein said catalyst has quaternary phosphonium group immobilized on a silicon resin, silica, inorganic supporter or organic polymer.

5. The process for preparing organosilicon compounds according to any one of claims 1, 2, or 3, wherein a co-catalyst is further used.

6. The process for preparing organosilicon compounds according to any one of claims 1, 2, or 3, wherein an amount of catalyst used is 1–100% by mole of the compound of formula III.

7. The process for preparing organosilicon compounds according to claim 1, wherein said reaction temperature is 10–250° C.

8. The process for preparing organosilicon compounds according to claim 1, wherein an amount of the hydrochlorosilane of formula II used is equivalent to or more than an amount of the organic halides of formula III.

9. The process for preparing organosilicon compounds according to claim 1, wherein said reaction is carried out in an organic solvent.

10. The process for preparing organosilicon compounds according to claim 1, wherein said reaction is carried out in neat condition.

11. The process for preparing organosilicon compounds according to claim 6, wherein said amount of catalyst used is 5–20% by mole of the compound of formula III.

12. The process for preparing organosilicon compounds according to claim 7, wherein said reaction temperature is 130–200° C.

13. The process for preparing organosilicon compounds according to claim 8, wherein said amount of the hydrochlorosilane of formula II used is 2–4 fold of an amount of the organic halides of formula III.

14. The process for preparing organosilicon compounds according to claim 9, wherein said organic solvent is selected from the group consisting of benzene, toluene, hexane, tetrahydrofuran, and acetonitrile.

* * * * *

UNITED STATES PATENT AND TRADEMARK OFFICE
CERTIFICATE OF CORRECTION

PATENT NO. : 6,392,077 B1
DATED : May 21, 2002
INVENTOR(S) : Il-Nam Jung et al.

It is certified that error appears in the above-identified patent and that said Letters Patent is hereby corrected as shown below:

Title page,
Item [30], Foreign Application Priority Data,
"00-64692" should read -- 2000-64692 --.

Item [74], *Attorney, Agent or Firm*, "Fitzpatrick, Cella, Harper, & Scinto" should read -- Fitzpatrick, Cella, Harper & Scinto --.

Column 1,
Line 42, "hydrocarbons" should read -- hydrocarbon --.

Column 2,
Line 13, "have" should read -- has --;
Line 16, "previously" should read -- previous --;
Line 38, "catalized" should read -- catalyzed --;
Line 49, "catalyst" should read -- catalysts --; and
Line 59, "will" should read -- is --.

Column 3,
Line 23, "hydrocarbons" should read -- hydrocarbon --.

Column 5,
Line 66, "benyltriphenylphosphonium" should read -- benzyltriphenylphosphonium --.

Column 6,
Line 42, "con" should read -- cone --.

Column 7,
Line 2, "reacted" should read -- reacted at --.

Column 8,
Line 21, "Benyltributylphosphonium" should read -- Benzyltributylphosphonium --;
Line 23, "benyltributylphosphonium" should read -- benzyltributylphosphonium --;
Line 35, "Benyltributylphosphonium" should read -- Benzyltributylphosphonium --; and
Line 37, "benyltributylphosphonium" should read -- benzyltributylphosphonium --.

UNITED STATES PATENT AND TRADEMARK OFFICE
CERTIFICATE OF CORRECTION

PATENT NO. : 6,392,077 B1
DATED : May 21, 2002
INVENTOR(S) : Il-Nam Jung et al.

It is certified that error appears in the above-identified patent and that said Letters Patent is hereby corrected as shown below:

Column 10,
Line 4, "tyltrichlocorosilane" should read -- tyltrichlorosilane --; and
Line 5, "Cyclopentyltrichlocorosilane;" should read -- Cyclopentyltrichlorosilane; --.

Column 11,
Line 7, "3-(Chloropropyl)" should read -- ¶ 3-(Chloropropyl) --; and
Line 21, "1,3-bis(trichlorosily)propane" should read -- 1,3-bis(trichlorosilyl)propane --.

Column 12,
Line 36, "compounds" should read -- compound --;
Line 45, "compounds" should read -- compound --;
Lines 46, 54 and 58, "a" should be deleted;
Line 55, "aromatic;" should read -- aromatics --;
Line 57, "compounds" should read -- compound --;
Line 58, "aromatics" should read -- aromatic --;
Lines 61 and 66, "or" should be -- and --;
Line 63, "silicon" should read -- silicone --.

Column 13,
Line 2, "or" should read -- and --.

Signed and Sealed this

Twenty-first Day of January, 2003

JAMES E. ROGAN
*Director of the United States Patent and Trademark Office*